United States Patent [19]

Gebauer et al.

[11] 4,380,675
[45] Apr. 19, 1983

[54] 2,4-DIALKYL-2,6-HEPTADIENAL DERIVATIVES, A PROCESS FOR THEIR PREPARATION, AND FRAGRANT AND FLAVORING PRODUCTS MADE THEREWITH

[75] Inventors: Helmut Gebauer, Munich; Walter Hafner, Furth, both of Fed. Rep. of Germany

[73] Assignee: Consortium fur Elektrochemische Industrie GmbH, Munich, Fed. Rep. of Germany

[21] Appl. No.: 230,778

[22] Filed: Feb. 2, 1981

[30] Foreign Application Priority Data

Apr. 9, 1980 [DE] Fed. Rep. of Germany ....... 3013672

[51] Int. Cl.³ .............................................. C07C 47/21
[52] U.S. Cl. .................................. 568/448; 568/840; 568/849
[58] Field of Search ............... 568/449, 450, 459, 458, 568/420, 421, 448, 849, 873, 840

[56]  References Cited

U.S. PATENT DOCUMENTS

| 3,654,309 | 4/1972 | Thomas | 568/420 |
| 3,978,092 | 8/1976 | Ichikawa et al. | 568/420 |
| 4,010,210 | 3/1977 | Vrigorievick | 568/37 |
| 4,209,644 | 6/1980 | Ichikawa et al. | 568/420 |

FOREIGN PATENT DOCUMENTS 2439140  3/1975  Fed. Rep. of Germany ...... 568/459

OTHER PUBLICATIONS

Blanc et al. "Chem. Abstracts", vol. 60 (1964) p. 13134c.
"Helv. Chim. Acta." vol. 47(2) pp. 567–575 (1964).
Eschinasi et al. "Chem. Abstracts" vol. 62 (1965) p. 6520–6521.
Eschinasi et al. "Tetrahedron Letters" No. 47, pp. 3487–3494 Pergamon Press.
Boeckman et al. "Chem. Abstracts" vol. 81 (1974) p. 37194q.
Boeckman et al. "Tetrahedron Letters" (1974) No. 11 pp. 917–920 Pergamon Press.
Vig et al. "Chem. Abstracts" vol. 72 (1970) p. 32036u.
Vig et al. "Indian Journal of Chemistry" vol. 7, (1969) pp. 1111–1113.

*Primary Examiner*—Werren B. Lone
*Attorney, Agent, or Firm*—Allison C. Collard; Thomas M. Galgano

[57]  ABSTRACT

Compounds of the formula

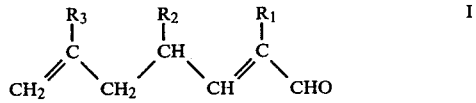

wherein $R_1$ and $R_2$ are equal or different aliphatic radicals, if desired, branched, and $R_3$ stands for H or $CH_3$. The invention also relates to a process for making these compounds and their use as fragrant and flavoring products.

3 Claims, No Drawings

2,4-DIALKYL-2,6-HEPTADIENAL DERIVATIVES, A PROCESS FOR THEIR PREPARATION, AND FRAGRANT AND FLAVORING PRODUCTS MADE THEREWITH

The invention relates to 2,4-dialkyl-2,6-heptadienal derivatives, a process for their preparation, and fragrant and flavoring products made therewith. The invention also relates to modified derivatives thereof wherein hydrogen is added to at least one double bond.

Up to the present, isoprenoid-like 2,6-dienes were obtained by isolation and, if necessary, by conversion of natural substances. Aldehydes of such a structure, e.g., citral, are frequently used as components of perfumes or as additives to food, as well as intermediates for the preparation of insecticides or pharmaceuticals.

Entirely synthetic productions required, up to now, mostly multi-stage processes, wherein expensive reactions such as the Wittig reaction and the use of metal-organic compounds, were indispensable.

It is an object of the invention to provide compounds useful for the above-mentioned purpose.

It is another object of the invention to provide simple, fully synthetic processes for the preparation of those compounds.

Other objects and advantages of the invention will be apparent from the following description.

These objects are obtained according to the invention by preparing compounds of formula I

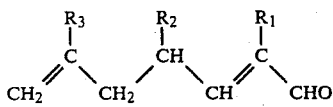

and modified species, in which hydrogen is added to at least one double bond wherein $R_1$ and $R_2$ are the same or different aliphatic radicals and, if desired, branched, and wherein $R_3$ stands for H or $CH_3$.

The process for preparing the new compounds is characterized in that compounds of the formula II

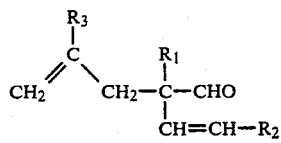

are subjected to a heat treatment of 80°–300° C., preferably 150°–250° C.

Surprisingly, these compounds undergo rearrangements with formation of the compounds according to the invention, in spite of various steric hindrances.

In order to avoid formation of cross-linked and oxidation products, it is frequently advantageous to carry out the heat treatment in the absence of air. Suitable measures are operating in a closed system, or by gassing the reaction mixture with inert gases e.g., nitrogen, argon, and the like.

Preferably, the temperature treatment according to the invention is carried out at pressures of about 1 bar. However, if desirable, lower or higher pressures may be used. When the synthesis is carried out with the compounds according to the invention which have bulky radicals $R_1$ or $R_2$, sometimes the higher temperatures lying within the mentioned range, and pressures up to 10 bars are advisable, in order to avoid prolonged reaction times. Otherwise, temperatures between 150° and 250° C. are preferred.

The starting materials may be obtained, in a manner known per se, by reacting aliphatic aldehydes with at least three carbon atoms with allyl- or methallyl-halides in phase-transfer catalyzed reaction (U.S. Pat. No. 4,196,151).

Alternatively, α-β-unsaturated aldehydes, as they may be obtained, e.g., by aldol condensations, can be used as primary products, from which the required starting compounds can be obtained by way of α-substitution reactions with allyl- or methallyl-halides, respectively; see U.S. Pat. No. 4,010,207.

A preferred method for producing the compounds according to the invention consists of a first step in which, in a manner known per se, β-γγ'-δ'-unsaturated aldehydes are prepared for reacting two moles aliphatic aldehyde having at least three carbon atoms with one mole allyl- or methallyl-halide in an organic/aqueous alkaline two-phase system, in the presence of phase-transfer catalysts. In a second step of the reaction the product is subjected to a temperature treatment ranging from 80° to 300° C., preferably 150° to 250° C.

According to the invention, in general, cis-transisomer mixtures are obtained (E and Z forms). E and Z forms can be qualitatively and quantitatively distinguished, e.g., by H-NMR-spectroscopy. In each case, the proportion of an isomer in the mixture is determined partly by the space requirement of the substituents $R_1$ and $R_2$; with bulky radicals, the equilibrium is, in general, shifting toward the Z-form.

According to the invention, mixtures of the isomers are used. However, if desired, the mixtures can be separated into their individual components by known methods, e.g., chromatography. The invention relates both to the isomer mixtures and the individual components.

Furthermore, the invention relates to compounds which are formed by hydrogen addition to at least one double bond, which can either be a carbon double bond and/or a carbonyl bond.

The addition of hydrogen to at least one double bond of the 2,4-dialkyl-2,6-heptadienals can be obtained in a known manner. With respect thereto, a distinction has to be made between selective and total hydrogenation. Examples for hydrogenation agents which act selectively on carbonyl are sodium boranate, lithium alanate and others. Total hydrogenation can be accomplished, e.g., in the presence of Raney nickel with molecular hydrogen.

By using less active catalysts of the platinum metals, treatment with molecular hydrogen will result in selective hydrogenation of the carbon double bond in the 6-position, while the double bond in the 2-position remains unchanged due to its protection by substituents.

The skilled artisan in this field moreover, knows the ways, for instance by a detour of acetal formation, to hydrogenate selectively the carbon double bonds, while the aldehyde group can be restored. Furthermore, the Tischtschenko reaction permits one to simultaneously obtain from the aldehyde the reduced form (alcohol) and the oxidized species (the acid).

Compounds are preferred, which in the 2- and 4-positions contain aliphatic substituents with 1 to 18 carbon atoms, if desired, branched. These substituents are derived from aldehydes with 3 to 20 carbon atoms, which, in turn, are obtainable from the corresponding fatty acids. Within this group, compounds with the same radicals $R_1$ and $R_2$ are preferred, because of the good yields. Because of their ready availability, compounds are especially preferred, in which $R_1$ and $R_2$ stand for radicals with 1–5 carbon atoms, which may be branched. The special preference of low-molecular compounds according to the invention is also due to their comparatively low boiling points, rendering them advantageous for use in perfumes and flavoring agents.

Examples of compounds according to the invention are: 2,4-dimethyl-2,6-heptadienal; 2,4-diethyl-2,6-heptadienal; 2,4-di-n-propyl-2,6-heptadienal; 2,4-di-isopropyl 2,6-heptadienal; 2,4-di-n-butyl-2,6-heptadienal; 2,4-isobutyl-2,6-heptadienal; 2,4-di-n-pentyl-2,6-heptadienal; 2,4-di-iso-pentyl-2,6-heptadienal; 2,4-neopentyl-2,6-heptadienal; 2,4-di-n-hexyl-2,6-heptadienal; 2,4-di-n-heptyl-2,6-heptadienal; 2,4-di-n-octyl-2,6-heptadienal; 2,4-di-n-nonyl-2,6-heptadienal; 2,4-di-n-decyl-2,6-heptadienal; 2-methyl-4-ethyl-2,6-heptadienal; 2-methyl-4-propyl-2,6-heptadienal; 2-ethyl-4-methyl-2,6-heptadienal; 2-propyl-4-methyl-2,6-heptadienal; 2-ethyl-4-propyl-2,6-heptadienal; 2-propyl-4-ethyl-2,6-heptadienal; 2,4-dimethyl-2,6-heptadienol; 2,4-diethyl-2,6-heptadienol; 2,4-n-propyl-2,6-heptadienol; 2,4-di-iso-propyl-2,6-heptadienol; 2,4-di-n-butyl-2,6-heptadienol; 2,4-dimethyl-heptanol; 2,4-diethyl-heptanol; and 2-methyl-4-propyl-heptanol.

The compounds according to the invention are obtained by simple chemical operations from basic chemicals industrially available—namely, aliphatic aldehyde and allyl- or methallyl-halides, respectively. For such isoprenoid-like aldehydes or their hydrogenated derivatives, there exists a great number of useful applications, for instance, when they are used as components for flavoring agents or additives to food, one can obtain citrus-like, woody, or flour-like aromas. They are, moreover, of particular interest for making intermediates for insecticides, attractants, and juvenile hormones. In addition, they serve as monomers for making valuable polymers.

In the following examples, the process of the present invention will be more fully described, which are given by way of illustration and not of limitation.

EXAMPLE 1

Preparation of 2,4-dimethyl-2,6-heptadienal (a) 2-Allyl-2-methyl-3-pentenal.

A four-neck one liter flask equipped with stirrer, thermometer and reflux cooler is first filled with 160 g of 5% sodium hydroxide solution, 50 ml water, and 10 g tetrabutylammonium iodide, and heated to 60° C. Then, a mixture of 61.5 ml (0.75 mol.) allyl chloride, and 72 ml (one mol.) propionaldehyde is rapidly added dropwise so that a temperature of 65° to 70° C. will be obtained (during about 1 hour). The reaction mixture is maintained for another 2 hours at 60° C. and, subsequently, 100 ml water are added, while stirring shortly. The phases are then separated, the aqueous phase is twice extracted with 100 ml toluene and the combined organic phases are finally fractionated, after withdrawal of the solvent, over a Vigreux column of 30 cm length. Obtained are 31.7 g (46% of the theoretical amount calculated on the aldehyde) of 2-allyl-2-methyl-3-pentenal. B.p.$_{12}$: 57°–60° C.

(b) 2,4-Dimethyl-2,6-heptadienal.

In a 100 ml flask with reflux cooler, 61 g 2-allyl-2-methyl-3-pentenal are heated to 160° C. while nitrogen is slowly passed through until complete rearrangement has been obtained (GC-control). After about 14 hours, subsequent fractionation yields 39.8 g of a cis-trans isomer mixture (78% of the aldehyde) of 2,4-dimethyl-2,6-heptadienal. Colorless oil, B.p.$_{11}$: 72°–75° C.; 92% E-form and 8% Z-form.

EXAMPLE 2

Preparation of 2,4-diethyl-2,6-heptadienal (a) 2-Allyl-2-ethyl-3-hexenal.

Into a 50 liter glass apparatus equipped with stirrer, reflux cooler and dropping funnel, 6 kg of 50% sodium hydroxide solution, 2.5 l water, 8 l toluene and 200 g tetrabutylammonium iodide are introduced first. Within 2 hours, 4,6 l (50 mol.) butyraldehyde and 3 l (37.5 mol.) allylchloride are added while stirring. The reaction vessel temperature is maintained at 62° to 68° C. After 7 hours of after-reaction at the same temperature, the aqueous phase is separated. The organic phase is twice washed with 3 l of water, each time, and finally distilled over a 140 cm column filled with packing material. Yield 2.82 kg calculated on the aldehyde used (68% of the theoretical amount). Colorless oil, B.p.$_{12}$: 82°–83° C.

(b) 2,4-Diethyl-2,6-heptadienal.

128 g aldehyde from compound (a) are heated under nitrogen for 10 hours to 180° C. The GC-control shows almost quantitative reaction. By subsequent distillation over a Vigreux column of 30 cm length, 110 g (86% of the theoretical amount) of an isomer mixture are obtained consisting of 96% E-form and 4% Z-form. Colorless oil, B.p.$_{12}$: 92°–93° C.

EXAMPLE 3

Preparation of 2,4-di-n-propyl-2,6-heptadienal (a) 2-Allyl-2-n-propyl-3-heptenal.

Into a 2 liter four-neck flask with stirrer, thermometer, dropping funnel and reflux cooler, 400 g 50% sodium hydroxide solution, 125 ml water, 400 ml toluene and 25 g tetrabutyl ammoniumbromide are first introduced. To this, a mixture of 280 ml (2.5 mol.) n-valeraldehyde and 155 ml (1.9 mol.) allylchloride are added dropwise within a 35 minute period, while stirring at a temperature of 70° to 80° C. After 6 hours of after-reaction at 80° C., the phases are separated, the organic phase is washed with 100 ml water and distilled over a Vigreux column of 30 cm length. The reaction product is obtained as colorless oil of B.p.$_{12}$: 109° to 111° C. Yield: 165 g (68% of the theoretical amount, calculated on aldehyde used).

(b) 2,4-Di-n-propyl-2,6-heptadienal.

80 g aldehyde obtained from (a) are heated in a glass flask in the absence of air while stirring for 14 hours at 185° C. to the almost quantitative conversion (GC-control). In the main fraction, 68.5 g (86% of the theoretical value) of a product were distilled which is a mixture of 80% of the E-form and 20% of the Z-form. Colorless oil, B.p.$_9$: 114° C.

EXAMPLE 4

Preparation of 2,4-di-i-propyl-2,6-heptadienal (a) 2-Allyl-2-i-propyl-5-methyl-3-hexenal.

Into a 2 liter four-neck flask with stirrer, thermometer, dropping funnel and reflux cooler, 400 g 50% sodium hydroxide solution, 125 ml water, 400 ml toluene, and 25 g tetrabutyl ammoniumbromide are first introduced. While stirring at a temperature of 65° C., a mixture of 376 ml (3.5 mol.) isovaleraldehyde and 155 ml (1.9 mol.) allylchloride are measured in during 45 minutes. After 4 hours after-reaction at the same temperature, the phases are separated, the aqueous phase extracted with 100 ml toluene, the combined organic phases dried with anhydrous sodium sulfate, and fractionated over a Vigreux column of 30 cm length. Yield 224 g (66% of the theoretical amount, calculated on aldehyde). Colorless oil, B.p.$_{0.01}$: 49° C.

(b) 2,4-Di-i-propyl-2,6-heptadienal.

100 g aldehyde obtained in (a) are heated in a glass flask to 180° C. in the absence of air while stirring. After 20 hours, the GC spectrum shows complete conversion. The following distillation yields 84 g (84% of the theoretical amount) of the desired product, isomer ratio 1:1. Colorless oil, B.p.$_{12}$: 104° to 106° C.

EXAMPLE 5

2,4-Di-ethylheptanol

Into a 0.5 liter shaking autoclave with glass insert, 33.2 g (0.2 mol.) 2,4-diethyl-2,6-heptadienal, 70 ml methanol and 3 g freshly prepared Raney nickel were introduced. The hydrogenation takes about 165 minutes after the pressure becomes constant. Subsequently, the catalyst is filtered off and after withdrawal of the solvent, distillation takes place in a water jet vacuum. The yield is 28 g, corresponding to 81.4% of the theoretical amount. B.p.$_{12}$: 109° C., colorless oil, fruit-like fragrance.

EXAMPLE 6

2,4-Dimethyl-2,6-heptadienol

Into a 250 ml two-neck flask with dropping funnel and reflux cooler, 1.1 g (0.029 mol.) LiAlH$_4$ in 100 ml of absolute ether are first introduced. While stirring, a solution of 13.8 g (0.1 mol.) 2,4-dimethyl-2,6-heptadienal in 40 ml absolute ether are added dropwise so rapidly that the mixture will boil moderately. After one hour's afterreaction and reflux, hydrolyzation with ice water takes place, and then diluted sulfuric acid is added for weak acidification. The phases are then separated and the organic phase is distilled in a water jet vacuum after drying with Na$_2$SO$_4$. The yield is 11.1 g corresponding to 79.3% of the theoretical amount. B.p.$_{12}$: 90° C., colorless oil, citrus-like, fruity fragrance.

What is claimed is:

1. A compound selected from the group consisting 2,4-dimethyl-2,6-heptadienal; 2,4-diethyl-2,6-heptadienal; 2,4-di-n-propyl-2,6-heptadienal; 2,4-di-iso-propyl-2,6-heptadienal; 2,4-dimethyl-2,6-heptadienol; and 2,4-diethyl-heptanol.

2. A fragrant substance containing a fragrancy-imparting amount of a compound in accordance with claim 1.

3. A flavoring substance containing a flavor-imparting amount of a compound in accordance with claim 1.

* * * * *